United States Patent [19]

Dormond et al.

[11] Patent Number: 4,839,822
[45] Date of Patent: Jun. 13, 1989

[54] COMPUTER SYSTEM AND METHOD FOR SUGGESTING TREATMENTS FOR PHYSICAL TRAUMA

[75] Inventors: Kenneth Dormond, Malvern; Robert J. Friedman, Paoli, both of Pa.

[73] Assignee: 501 Synthes (U.S.A.), Paoli, Pa.

[21] Appl. No.: 85,511

[22] Filed: Aug. 13, 1987

[51] Int. Cl.$^4$ ............................................. G06F 15/42
[52] U.S. Cl. .............................. 364/513; 364/413.02; 364/200; 364/274.5; 364/274.7; 364/275.7; 364/900
[58] Field of Search .............. 364/513, 413, 415, 300, 364/200 MS File, 900 MS File, 413.01, 413.02; 128/630

[56] References Cited

U.S. PATENT DOCUMENTS

| | | | |
|---|---|---|---|
| 4,130,881 | 12/1978 | Haessler et al. | 364/900 |
| 4,315,309 | 2/1982 | Coli | 364/200 |
| 4,489,387 | 12/1984 | Lamb et al. | 364/513 X |
| 4,517,468 | 5/1985 | Kemper et al. | 364/513 X |
| 4,591,983 | 5/1986 | Bennett et al. | 364/403 |
| 4,611,298 | 9/1986 | Schuldt | 364/900 |
| 4,642,782 | 2/1987 | Kemper et al. | 364/513 X |
| 4,644,479 | 2/1987 | Kemper et al. | 364/513 X |
| 4,648,044 | 3/1987 | Hardy et al. | 364/513 |
| 4,649,515 | 3/1987 | Thompson et al. | 364/900 |
| 4,654,852 | 2/1987 | Bentley et al. | 364/900 X |
| 4,656,603 | 4/1987 | Dunn | 364/900 |
| 4,658,370 | 4/1987 | Erman et al. | 364/513 |
| 4,730,259 | 3/1988 | Gallant | 364/415 X |
| 4,731,725 | 3/1988 | Suto et al. | 364/415 |
| 4,733,354 | 3/1988 | Potter et al. | 364/415 |

OTHER PUBLICATIONS

"Field Catagorization of Trauma Patients and Hospital Trauma Index", *Bulletin of the American College of Surgeons*, vol. 65, Feb. 1980, pp. 28-33.

Brochure entitled "Texas Instruments Personal Consultant TM Series Applications", Texas Instruments, 1987 (20 pages).

Gibson, Richard, "The Computer is in: More Doctors Use High-Tech Help for Diagnoses", *Wall Street Journal*, Jul. 8, 1987.

Nguyen, Tin A., Perkins, Walton A., Laffey, Thomas J. and Pecora, Deanne, "Knowledge Base Verification", *AI Magazine*, vol. 8, No. 2, (Summer 1987), pp. 69-75.

*Primary Examiner*—Joseph Ruggiero
*Attorney, Agent, or Firm*—Davis Hoxie Faithfull & Hapgood

[57] ABSTRACT

An expert system which provides one or more suggested treatments for a patient with physical trauma is disclosed. The system includes a computing device having a memory, a plurality of data bases in the memory, an application program and an inference engine program. The data bases include graphical illustrations of different types of physical trauma, and a knowledge base which contains treatment information. The application program is executed in the computing device and interactively displays a series of screens including at least some of the graphical illustrations, to elicit responses from the user concerning the specific types of physical trauma and specific characteristics of the patient. The inference engine program, which is also executed in the computing device, uses the knowledge base and information related to the responses elicited from the user, for selecting one or more suggested treatments. The application program presents the suggested treatments to the user after execution of the inference engine program.

17 Claims, 12 Drawing Sheets

COMPUTER SYSTEM AND METHOD FOR SUGGESTING TREATMENTS FOR PHYSICAL TRAUMA

REFERENCE TO MICROFICHE APPENDIX

Reference is hereby made to a microfiche appendix submitted herewith in accordance with 37 CFR 1.96(b). The appendix contains a computer program listing in the form of two microfiche having a total of 113 frames.

FIELD OF THE INVENTION

The present invention relates to the field of expert systems, and is directed to an expert system intended for use in treating various types of trauma, and in particular, orthopedic trauma.

BACKGROUND OF THE INVENTION

Artificial Intelligence (AI) is a branch of science resulting from the marriage of the cognitive and computer sciences. Computers, originally used for the manipulation of numbers (data) are now being used for the manipulation of ideas (knowledge). Trends and solutions can be inferred by the assimilation of observed facts just as numbers are added and subtracted to produce totals. Computer systems are being developed that exhibit thought processes previously ascribed only to humans.

The study of AI leads to insight regarding the human thought processes in addition to the development of practical systems to solve problems in the workpiece, the school and the home. The "expert system" is one method of obtaining such practical results with AI.

An expert system solves a problem through the manipulation of knowledge. The system consists of an inference engine and a knowledge base. The knowledge base is compiled from the experience of human experts in the field and encoded in a computer language suited for the description of ideas and principles. The inference engine controls the flow of the program, tracing solutions.

The inference engine has, in recent years, become a widely available product through a number of companies, including Gold Hill Computers Inc., of Cambridge, Massachusetts; Intellicorp, of Mountain View, California; Technology Applications, Inc., of Jacksonville, Florida; Teknowledge Inc., of Palo Alto, California; Neuron Data Inc., of Palo Alto, California; and Texas Instruments, of Austin, Texas. Two inference engines have been disclosed in U.S. Pat. Nos. 4,658,370 to Erman et al., and 4,648,044 to Hardy et al., both assigned to Teknowledge Inc.

Expert systems recently have found use in a variety of applications, such as in agriculture, chemistry, computer design, construction, engineering, finance, management, health care, manufacturing, and others. For example, in U.S. Pat. No. 4,591,983 Bennett et al., an expert system for use in inventory control is disclosed, and U.S. Pat. Nos. 4,517,468, 4,642,782, and 4,644,479, all to Kemper et al., each disclose a diagnostic system for monitoring an industrial system, such as a steam turbine generator power plant.

In the health care field, hospitals and medical laborities have used computers to analyze blood and run certain tests. Data bases have been established for recommending drug therapies for certain types of cancers. An expert system made by Cardinal Systems Inc., Minneapolis, Minnesota, includes standard textbooks data, and a graphical illustration of the sympathetic nervous system, for purposes of testing a diagnosis, and recommending therapeutic drugs. Other expert diagnostic and treatment systems are specific to a particular healthcare concern, such as, for example, a system called "Senex", specifically designed to aid in the treatment of breast cancer, and a system called "Hepatitis Assistant", designed for better diagnosis and treatment of hepatitis patients. Other health care systems are known to address the specific fields of epilepsy, poison control, childbirth and physical rehabilitation.

Although prior art expert systems have been designed to address a relatively wide range of health care concerns, little is known to have been done in the area of treatment of physical trauma. That is, it is beleived that none of the existing expert systems designed for health care applications have provided the ability to perform a consultation to help determine the optimal manner in which to treat a specific type of trauma. Such a system would be useful not only for suggesting a treatment, but also for providing a consultation session between an experienced surgeon and a learning surgeon.

OBJECTS AND SUMMARY OF THE INVENTION

It is therefore an object of the present invention to provide an expert system directed to the treatment of physical trauma.

It is a further object of the present invention to provide an expert system for the specific field of orthopedic trauma.

It is a further object of the present invention to provide an expert system which provides one or more treatment recommendations based upon specific classifications of physical trauma.

It is a further object of the present invention to provide an expert system capable of providing a treatment recommendation based upon specific classes of orthopedic trauma.

These objects are achieved by placing textbook information, such as fracture classifications, in a database, and expert information concerning orthopedic fractures in a knowledge base. In use, a fracture to to be treated is classified, and additional trauma information is obtained, along with some patient history. Initial treatment suggestions based upon the classification of the fracture are judged for appropriateness based upon supplemental clinical information, namely the expert information in the knowledge base. During inferencing, addititional information may be requested by the computer as needed. Treatment suggestions are presented in the order of preferred use.

The expert system in accordance with the present invention provides the user with one or more suggested treatments for a patient with physical trauma. The system includes a computing device having a memory, a plurality of databases in the memory, an application program and an inference engine program. The databases include graphic illustrations of different types of physical trauma and a knowledge base which contains treatment information. The application program is executed in the computing device and interactively displays a series of screens, including at least some of the graphical illustrations, to elicit reponses from the user concerning the specific type of physical trauma and specific characteristics of the patient. The inference engine program, which is also executed in the computing device, uses the knowledge base and information related to the responses elicited from the user, for selecting one or more suggested treatments. The application program presents the suggested treatments to the user after execution of the inference engine program.

In accordance with a more specific aspect of the present invention, the physical trauma consists of orthopedic fractures.

BRIEF DESCRIPTION OF THE DRAWINGS

These and other objects, aspects and embodiments of the present invention will now be described in more detail with reference to the following drawing figures, of which.

DETAILED DESCRIPTION OF THE INVENTION

Figure 1:
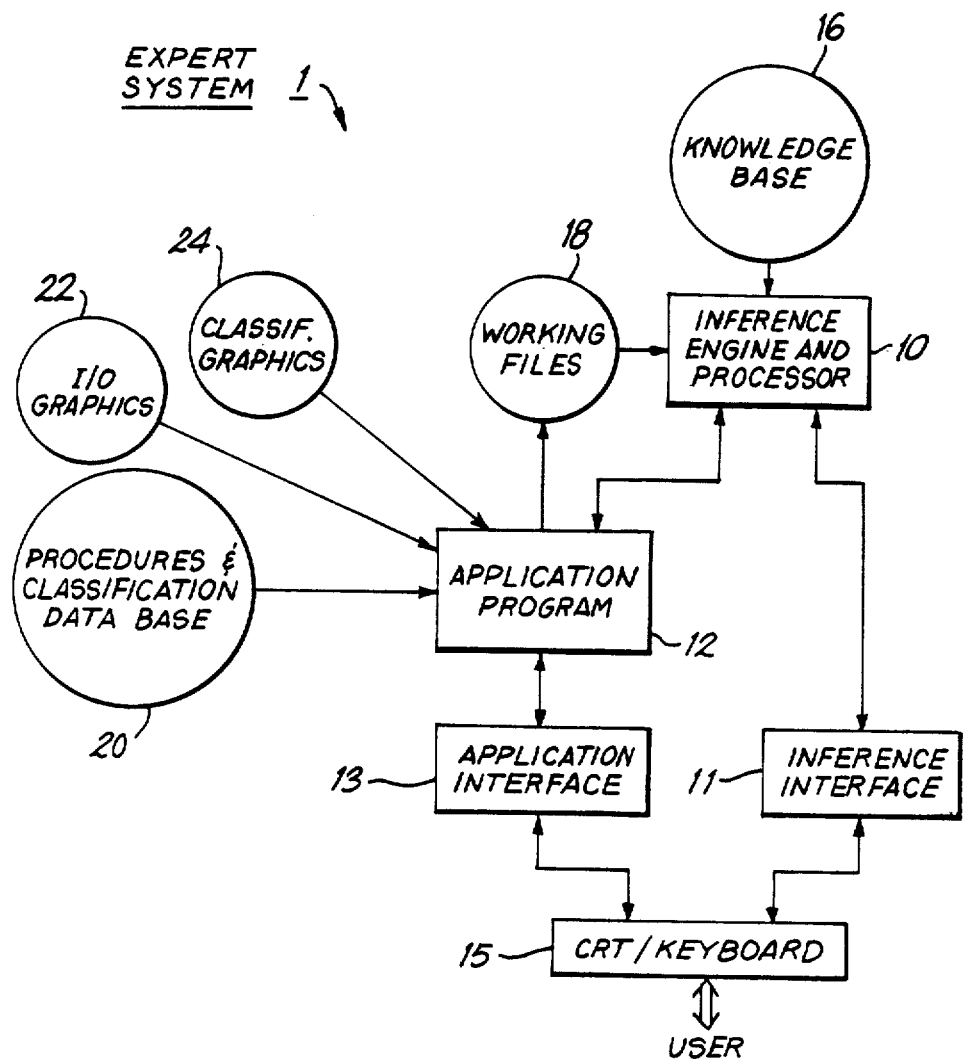
FIG. 1 is a diagram illustrating the structure of the expert system in accordance with the present invention.

The expert system in accordance with the present invention will be described with initial reference to FIG. 1. The expert system 1, includes an inference engine and processor 10, inference interface 11, application program 12 and application interface 13. The inference engine and processor 10 functions as in inference engine, under the control of an inference engine program, and also executes the application program 12, when necessary to perform application program functions, under the overall control of the inference engine. Communication between the expert system and the user is by way of a CTR/keyboard 15 and through the inference interface 11, for communicating with the inference engine and processor 10, and by way of application interface 13, for communicating with the application program 12. The inference engine and processor 10 can be selected from one of the available expert system packages identified above, for example, the Texas Instruments Personal Consultant TM Plus. An advantage of such systems is their ability to run on the commonly available 80286 or 80386 DOS-based personal computers.

The inference engine and processor 10 receives information from two data bases, namely a knowledge base 16, and a data base of working files 18 which are generated by the application program 12, based on information elicited from the user.

The knowledge base 16 includes a collection of rules and parameter descriptions, upon which one or more preferred treatment techniques are based. The information within the knowledge base is based on information from experts within the relevent field, in this case physical trauma, and in particular, orthopedic fractures. The working files 18, comprised of files referred to as PATIENT, DISEASE, TRAUMA and TISSUE, reflect specific information about a patient, including, for example, the patient's specific trauma, characteristics of the surrounding tissue, patient information such as height, weight, and the like, and information as to any pre-existing conditions, such as osteoporosis.

The knowledge base 16 permanently exists within the expert system, although it should be updated periodically in accordance with currently available expert knowledge. The working files 18, on the other hand, are specific to each patient and injury, and therefore must be created with each use of the expert system. In accordance with the present invention, a procedures and classification data base 20, input-output graphics 22 and classification graphics 24, are provided for the purpose of gathering the requisite patient and trauma information from the system user, and assembling that information into the working files 18. The procedures and classification description data base 20 includes, for each classification of trauma, such as orthopedic fractures, one or more initially recommended treatments and a short description of the orthopedic fracture. The initial procedures are based on textbook, and perhaps expert information, and are used by the inference engine as a starting point from which to determine a final group of recommended procedures. Also included in the data base 20 is a hierarchy of treatment procedures, a compilation of characteristics of each class of fracture, and a compilation of characteristics associated with pre-existing diseases and other trauma that the patient may exhibit. These files will be described in more detail below.

The input-output graphics 22 are provided as part of the expert system to elicit responses to a series of questions relating to the patient and trauma. The classification graphics 24, are based on the particular classes of trauma which the expert system addresses. In accordance with the present example, namely that of orthopedic fractures, the classification graphics 24 are based upon specific types of orthopedic fractures assembled from textbook and similar data. Two such sources of information are M. E. Müller, M. Allgower, R. Schnieder and H. Willenegger, MANUAL OF INTERNAL FIXATION (Berlin, Heidelberg, New York: Springer-Verlag, 2nd ed. 1979), and M. E. Müller, S. Nazarian and P. Koch, CLASSIFICATION AO DES FRACTURES, TOME I: LES OS LONGS (Berlin, Heidelberg, New York: Springer Verlag, August 1987).

The input-output graphics 22 and classification graphics 24, form the screens illustrated in FIGS. 2-17. It will be appreciated that these screens are exemplary and that other screens, which elicit the proper information, may be equally suitable. Also, the order in which the screens are displayed may be changed as necessary. Finally, although the subject matter of the screens relates to orthopedic fractures, the same or similar techniques may be used to gather information as to other types of trauma as well.

The application program, the knowledge base and the procedures and classification data base, produced in accordance with the specific example of the present invention described herein, are set forth in the microfiche appendix.

The operation of the expert system in accordance with the present invention will now be described with reference to FIGS. 2–17. Initially, it will be assumed that the expert system has begun to execute the application program, in a manner which will be described in more detail below.

Figure 2:
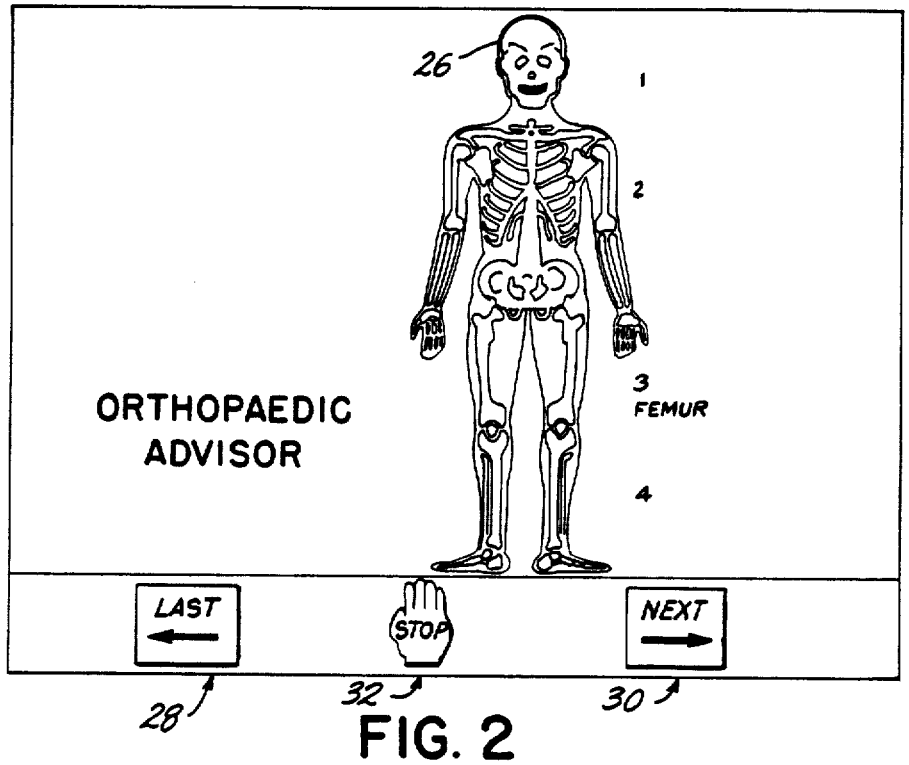
FIGS. 2 through 15 illustrate examples of screens which may be displayed in order to elicit information concerning characteristics of an orthopedic fracture and the patient, from the user of the system.

FIG. 2 is an illustration of the first of the screens provided by I/O graphics 22. As shown in FIG. 2, the expert system is called ORTHOPEDIC ADVISOR. The screen of FIG. 2 provides a "menu", namely a view of the primary bones in the human body, from which the user can select the particular bone which has been fractured. This can be done through the use of any well-known input technique, such as a touch-screen input, or through the movement of a cursor (not shown) by way of a mouse or cursor keys. The application program, provided in the microfiche appendix, supports the use of touch-screen technology and cursor movement through a mouse input or cursor keys. The user will either touch the screen at the location corresponding to the bone under study or move the cursor to that bone, in order to input that information into the application program. In the present example, the selected bone will be the upper long bone of the leg, namely the femur.

Also provided as part of the screen shown in FIG. 2 are locations on the screen, designated by reference numerals 28, 30 and 32, commonly called "icons", which may be selected by the user in order to perform the stated fucntions. For example, icon 28 which bears the legend "last", can be selected by the user either by touching the icon or by positioning the cursor over the icon, in order to instruct the application program to display the previous screen. Similarly, icon 30, which bears the legend "next", may be selected by the user to select the next screen, and icon 32, which bears the legend "stop", may be selected to terminate the program at this point. Each of these icons appears in the screens shown in FIGS. 2 through 16, and since their function is the same, further reference will not be made thereto.

Figure 3:
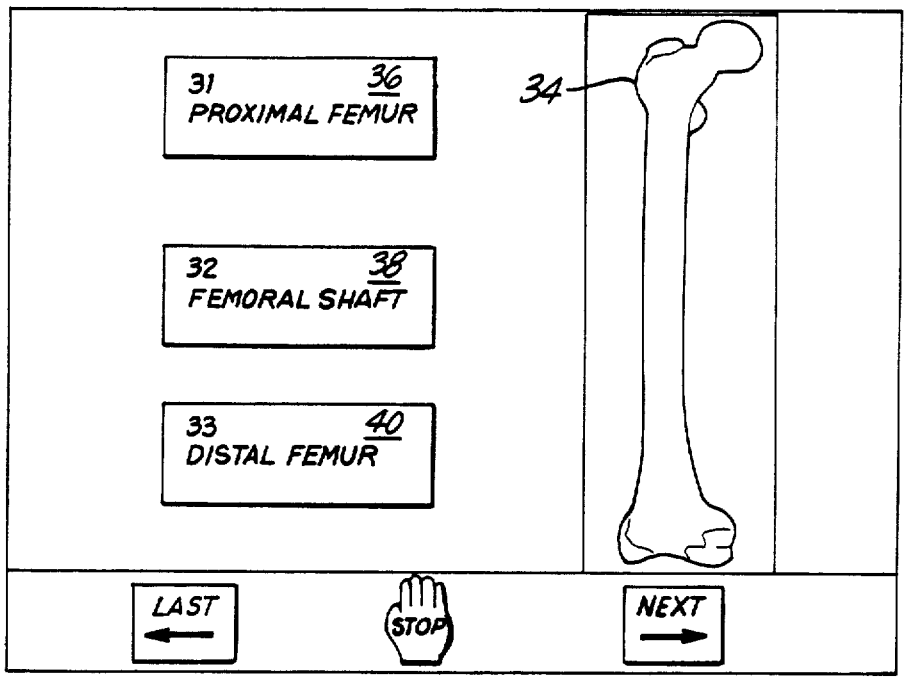

The femur having been selected, the application program displays the screen illustrated in FIG. 3, either automatically upon selection of the particular bone, or in response to selection of icon 30 for the next screen. The screen illustrated in FIG. 3 shows the selected bone, namely the femur, in isolation, and requests the user to select the portion of the femur which has been fractured. This can be accomplished by having the user either touch or move the cursor to the affected portion of the femur 34, or by having the user touch or move the cursor to any one of three areas 36, 38 or 40, to select the proximal femur, the femoral shaft, or the distal femur, respectively. The two-digit number illustrated in the upper left-hand corner of the areas 36, 38 or 40 designate the numerical classification of the site of the fracture, according to a coding scheme used by the procedures and classification data base 20.

Figure 4:
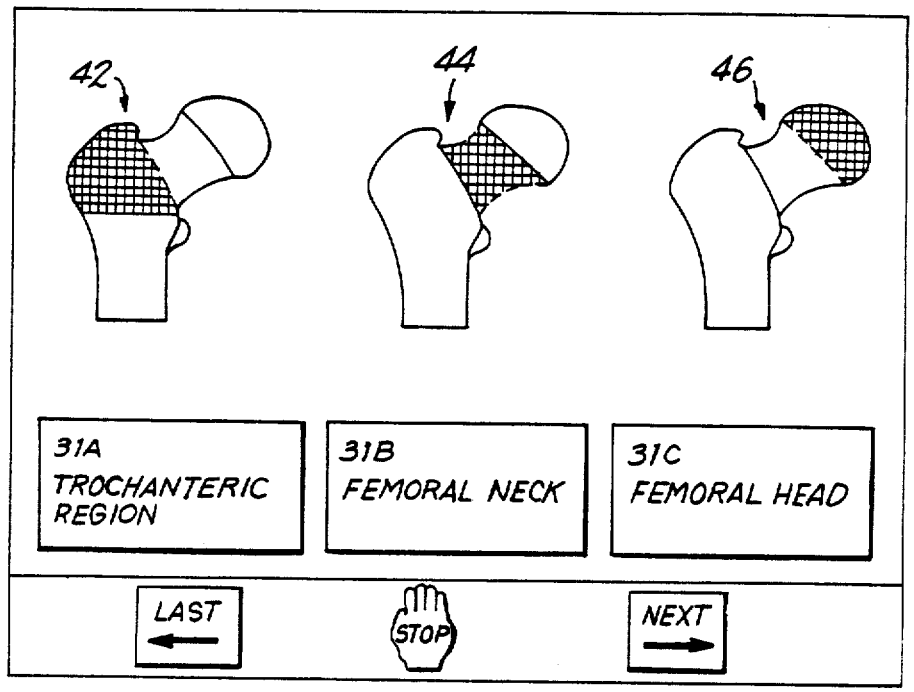

After havig selected the affected portion of the relevent bone, in this example the proximal femur, the screen illustrated in FIG. 4 is displayed, and the user is requested to select the affected region of the proximal femur, namely the (i) trochanteric region, (ii) the femoral neck, (iii) the femoral head, classifed as locations 31*a*, 31*b* and 31*c*, respectively. As shown in FIG. 4, three illustrations 42, 44 and 46 of the proximal femur are illustrated, each with cross hatching on the respective region, namely the trochanteric region in illustration 42, the femoral neck in illustration 44 and the femoral head in illustration 46. In this manner, the user continues as before, by simply selecting the illustration that corresponds to the fracture under study. In accordance with the present example, the femoral neck is selected as the region of fracture, and in response to that selection, the next screen, illustrated in FIG. 5, is displayed.

Figure 5:
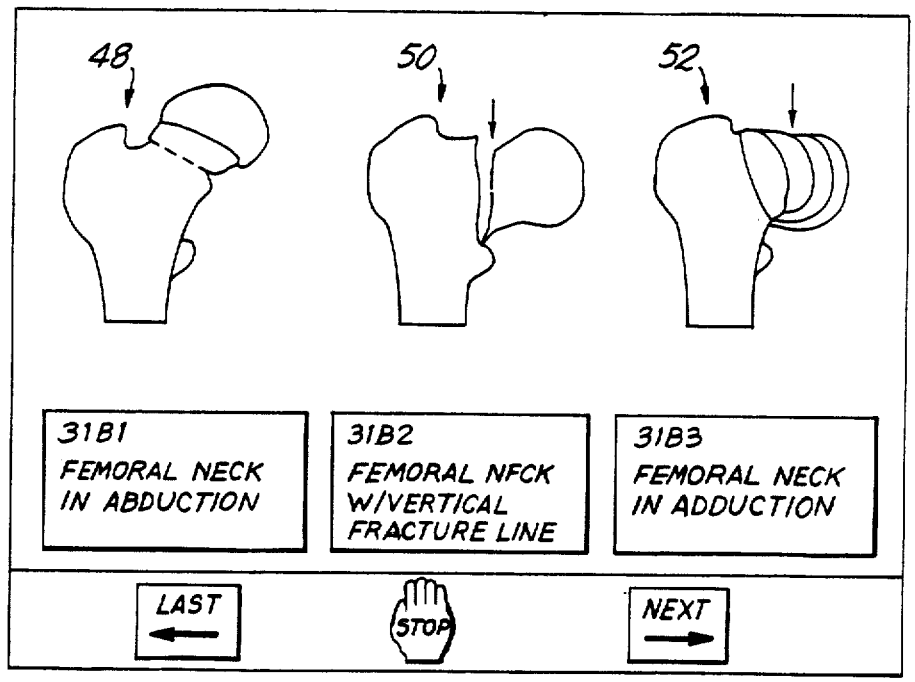
Figure 6:
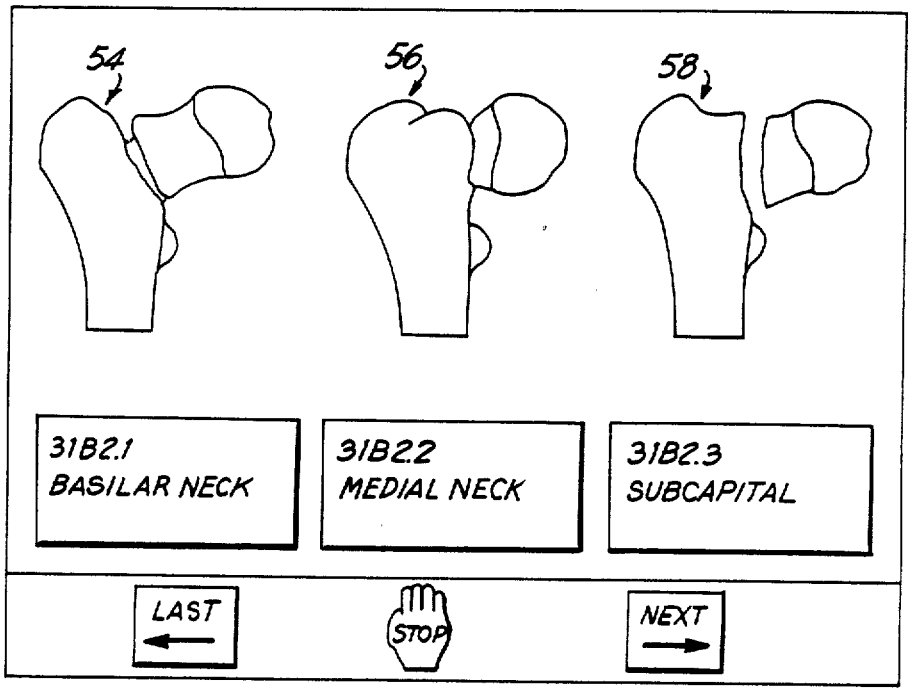

FIG. 5 illustrates three possible types of fractures of the femoral neck, namely the femoral neck in abduction (classification 31B1), the femoral neck with a vertical fracture line (classification 31B2), and the femoral neck in addition (classification 31B3). These classifications of specific fracture types are taken from the relevent body of knowledge on the subject of orthopedic fractures, such as the treatises by M. E. Müller et al., referred to above. As before, three illustrations 48, 50 and 52 are provided for the respective fracture classifications, in order to assist the user in selecting the appropriate classification. The user selects the type of fracture experience by the patient, which in this example is the femoral neck with vertical fracture line (classification 31B2). In response, the screen illustrated in FIG. 6 is displayed, illustrated three different types of femoral neck fractures with vertical fracture lines, specifically, a fracture of the basilar neck (classification 31B2.1), the medial neck (classification 31B2.2) and a subcapital fracture (classification 31B2.3). Three illustrations 54, 56 and 58 are provided in order to assist the user in selecting the appropriate type of fracture. In the present example, the medial neck (classification 31B2.2) is selected, and in response, the screen illustrated in FIG. 7 is displayed.

Figure 7:
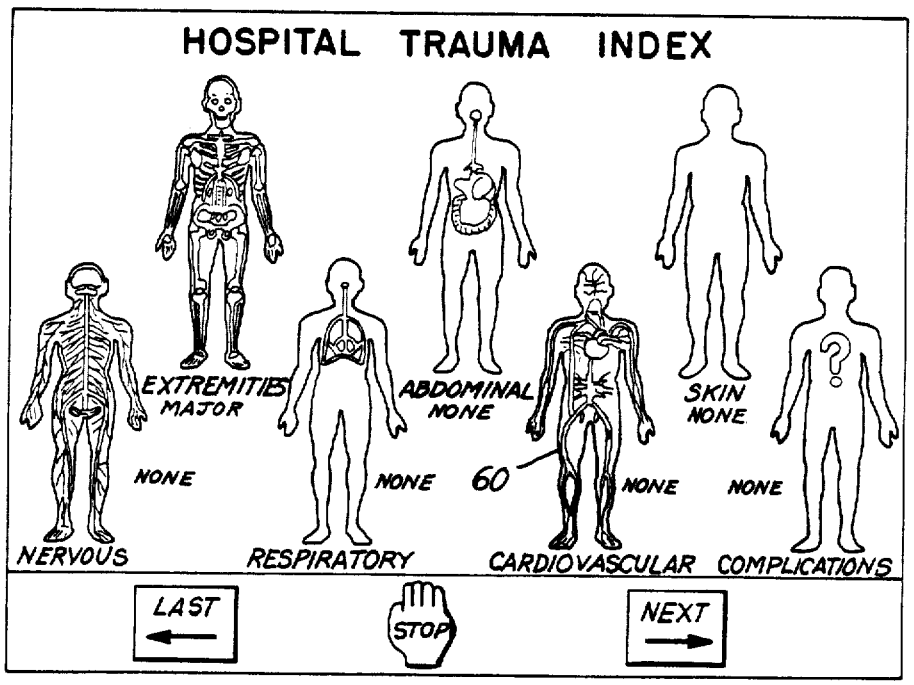
Figure 8:
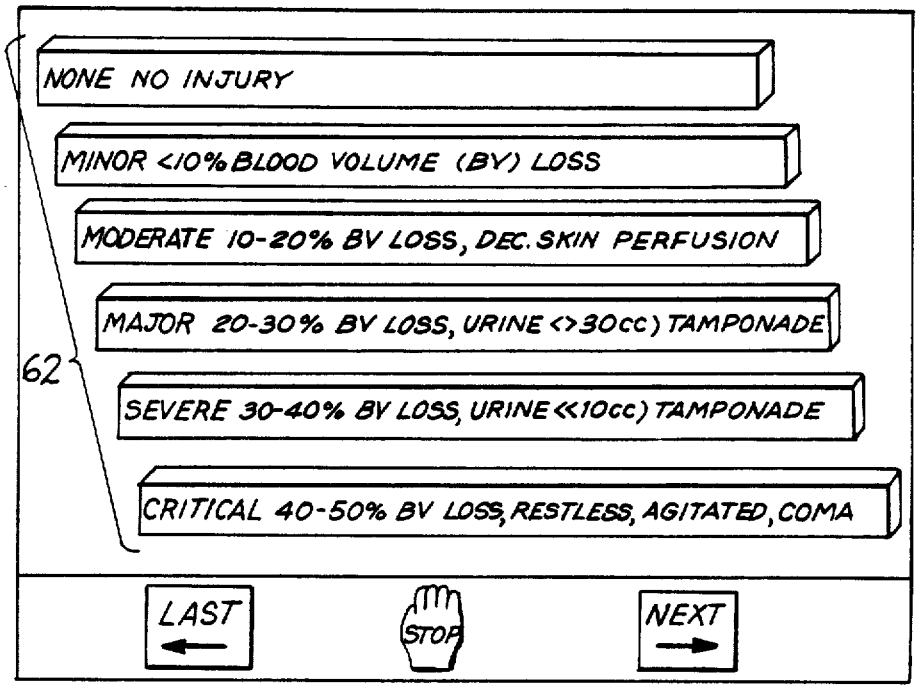

The screen illustrated in FIG. 7, which is generated in accordance with the graphics information in I/O graphics 22, requests that the user provided information as to any other trauma that the patient has experienced. For example, if the patient has lost blood, the user would select icon 60 to indicate cardiovascular trauma. In response to this selection, the screen illustrated in FIG. 8 is displayed and the user indicates the severity of blood loss, by selecting one of the choices 62. After making such a selection, the screen illustrated in FIG. 7 is again displayed, and a legend indicating the severity of cardiovascular trauma will appear next to icon 60. The user can then select other types of trauma, if applicable. This information is placed into the file TISSUE, in the working files 18, and is also used by the application program to arrive at an injury severity score (ISS), which is similarly placed in the file TISSUE. The calculation of the ISS is based on the technique disclosed in the article by the American College of Surgeons Committee on Trauma, entitled "Field Catagorization of Trauma Patients and Hospital Trauma Index", BULLETIN OF THE AMERICAN COLLEGE OF SURGEONS, Vol. 65, February 1980, pp. 28–33.

Figure 9:
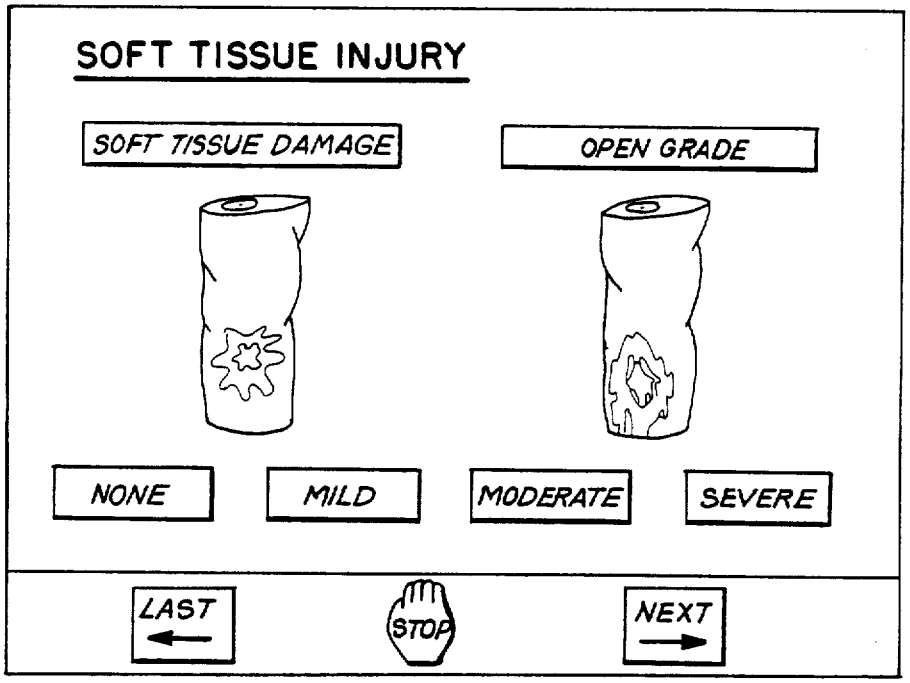

The next screen displayed is illustrated in FIG. 9 in which the user specifies the damage to the soft tissue surrounding the fracture and the open grade. This information also goes to the file TISSUE.

Figure 10:
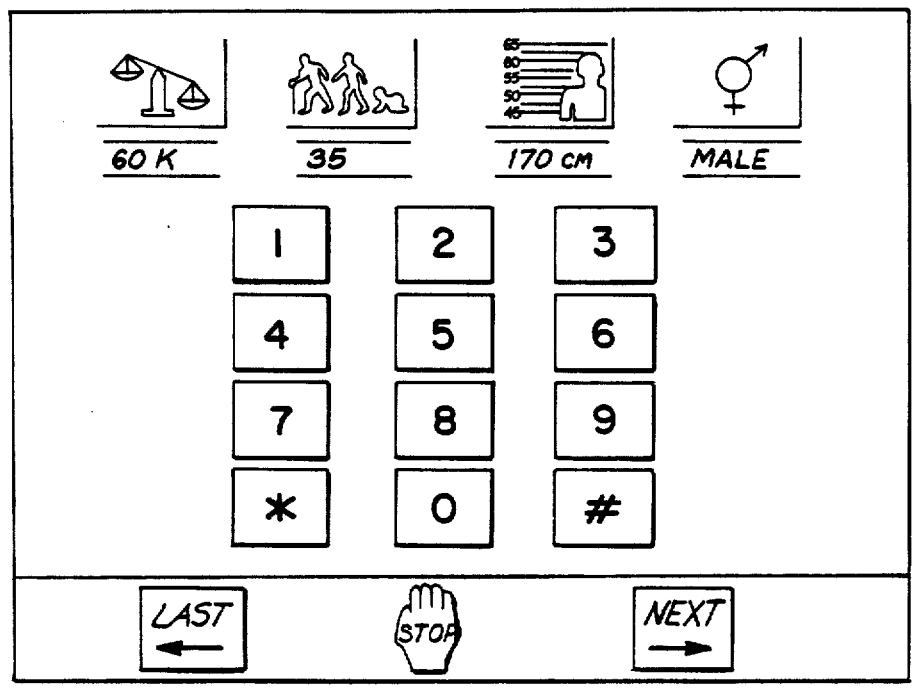
Figure 11:
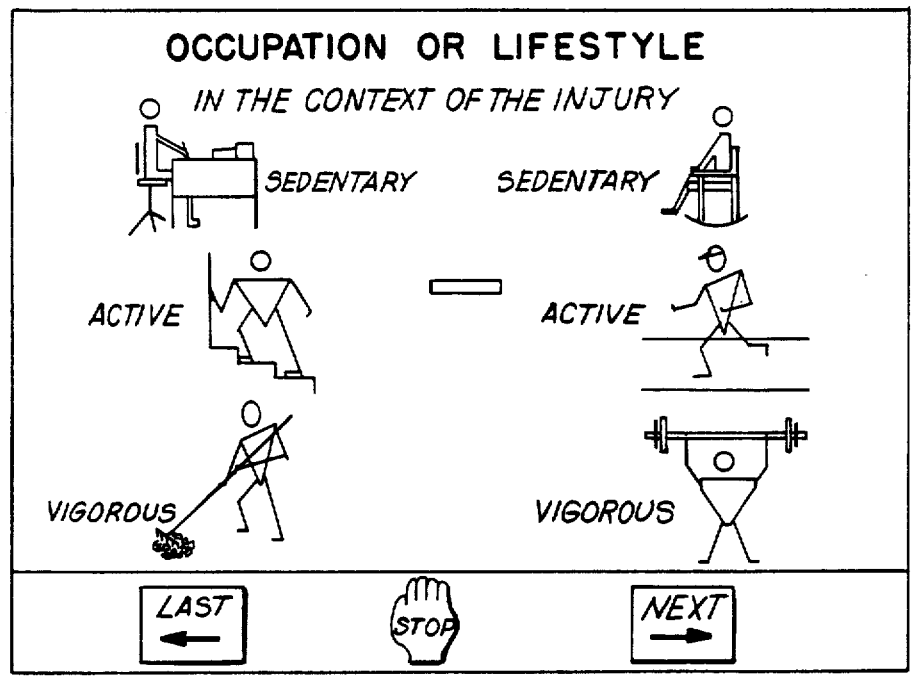

The screen illustrated in FIG. 10 is then displayed and the user indicates the patient's weight, age, height and sex. In this example, the patient weighs 60 kilograms, is 35 years old, is 170 centimeters tall and is male. This screen readily lends itself to touch-screen applications, but can also be used with cursor movement as well. The next screen, shown in FIG. 11, requests the user to input information concerning the patient's occupation or lifestyle, in the context of the injury, i.e., whether the patient is sedentary, active or vigorous. In this example, the patient is considered "active". The information elicited from the user by the screens shown in FIGS. 10 and 11 is placed in the PATIENT file in the working file 18.

Figure 12:
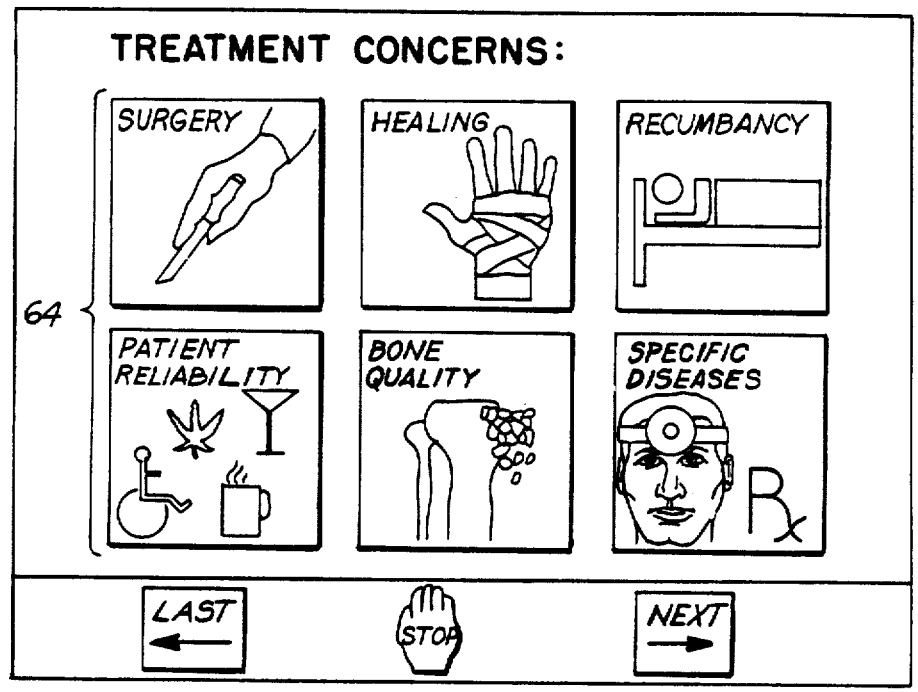

The next screen, shown in FIG. 12, requests the user to indicate any pre-existing illnesses that the patient might have, or other treatment concerns about the patient, since such considerations could affect the patient's ability to tolerate surgery, to heal properly, to remain convalescent (recumbency), or to follow instructions, for example. Six icons 64 designate selections of the following treatment concerns: surgery, healing, recumbency, patient reliability, bone quality and specific diseases. The first five of these treatment concerns are used by the application program to enter information, if applicable, into the file DISEASE in the working files 18. The sixth health concern, namely SPECIFIC DISEASES, elicits information from the user to determine whether any of the patient's pre-existing diseases would cause one of the first five health concerns, and that information would be placed into the file DISEASE, as well.

Figure 13:
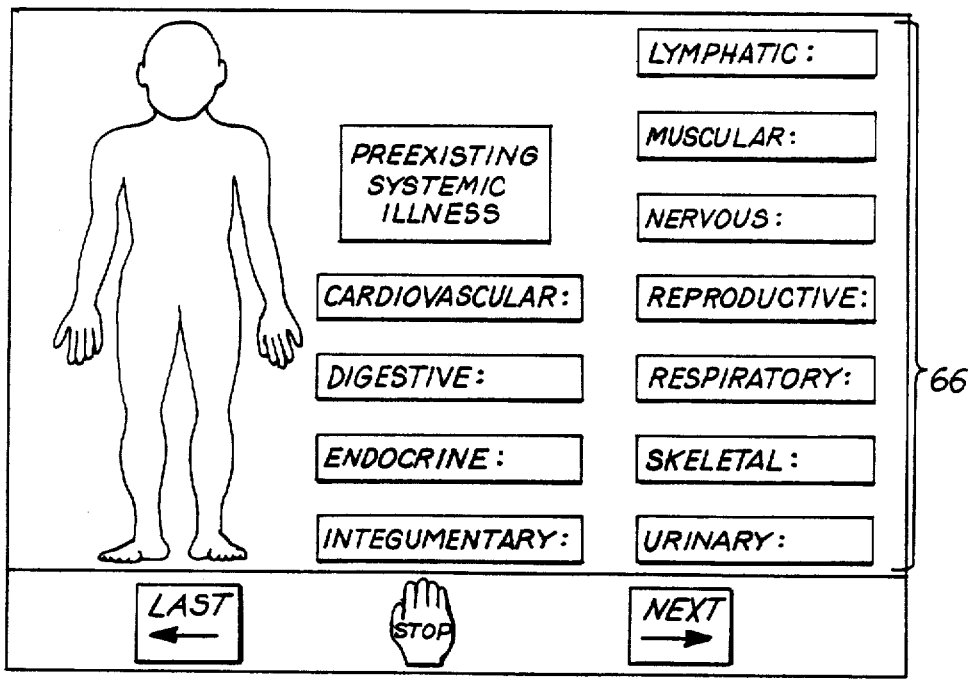
Figure 14:
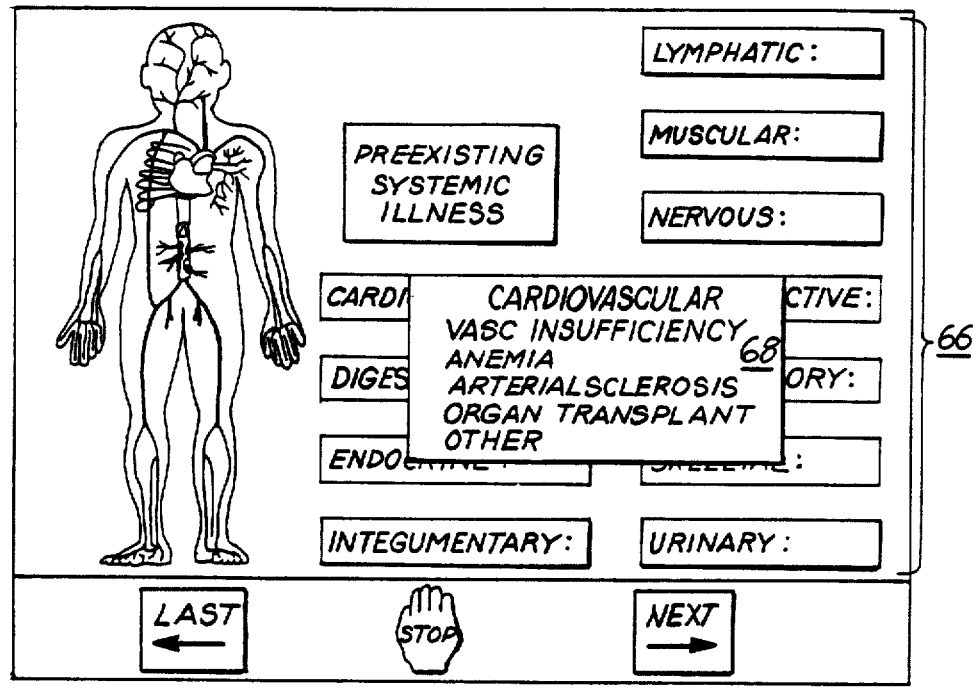

Specifically, when the user selects SPECIFIC DISEASES as a treatment concern, the application program displays the screen illustrated in FIG. 13 and requests that the user indicate, using icons 66, the physiological system associated with the patient's specific illness. In this example, the cardiovascular system is selected, and in response to that selection, a menu 68, FIG. 14, is displayed, and the user indicates one of the particular types of specific cardiovascular diseases. In this case, vascular insufficiently is selected. In response to this selection, the application program inquires of the procedures and classification data base 20 to see what specific treatment concerns are caused by vascular insufficiency. Using the DISEASE data base in the procedures and classification data base 20 (a copy of which is provided in the microfiche appendix), it is determined that vascular insufficiency causes a surgery concern with a 50 percent certainty factor. Thus, in response to selecting vascular insufficiency, the application program displays the screen illustrated in FIG. 15, to inform the user of the surgery concern. Alternatively, any of the surgery, healing, recumbency, reliability and bone quality concerns can be input directly through the use of the first five icons 54, FIG. 12.

Figure 15:
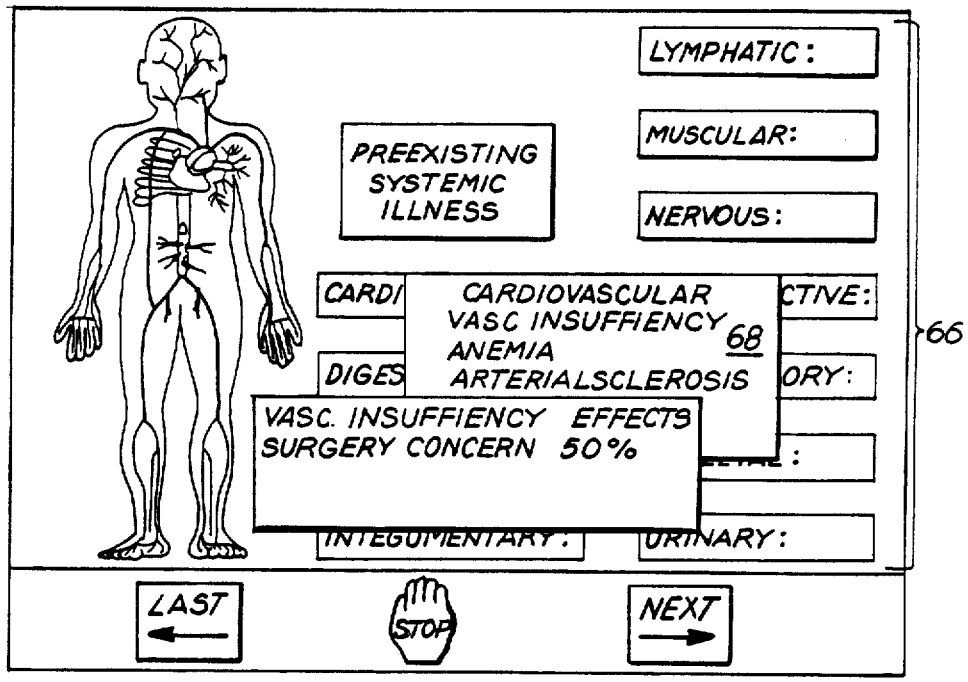

After entering the information concerning treatment concerns, the user can now instruct the expert system to proceed with the consultation, by selecting the NEXT icon in FIG. 15. In response, the inference engine 14, FIG. 1, applies the rules of the knowledge base 16, to the information contained within the working files 20 concerning the specifics of the patient and the orthopedic fracture. In the event that further information is required, for a particular set of inputs, the inference engine may generate one or more further inquires through the expert system interface 11, in order to gather the additional data from the user. For example, the expert system may inquire as to whether the injury resulted from a simple fall, from which the inference engine might infer that the patient is osteoportic, if such information is considered to be important.

Figure 16:
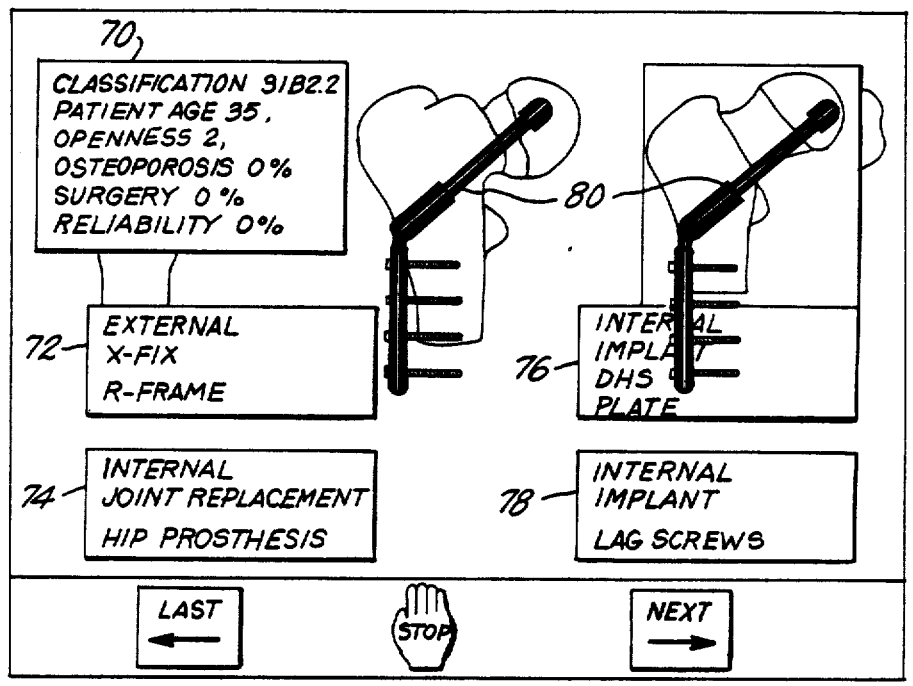
FIG. 16 illustrates a sample screen which can be used to illustrate to the user of the system the treatments for the particular orthopedic fracture and patient.

When the inference engine has gathered all the necessary information, it completes its tasks by achieving certain "goals", and then returns temporary control to the application program. A screen is then displayed, as illustrated in FIG. 16, and includes a table 70 which shows the classification of the fracture, and selected chatacteristics of the patient and trauma. In addition, four choices 72, 74, 76 and 78 are displayed as the treatments selected by the inference engine, for this specific case. These treatments may be ordered in terms of the most to least highly suggested, either by positional order, as displayed, or by a numerical or alphabetic indication by each treatment. In this case, the suggested procedures for this patient are an A-frame, a hip prosthesis, a DHS TM implant and lag screws. Additionally, the user at this point, by selecting a particular one of the recommended treatments, for example the DHS TM implant (the treatment indicated by the reference numeral 76), the application program will actually show the DHS TM implant 80 in place.

Figure 17:
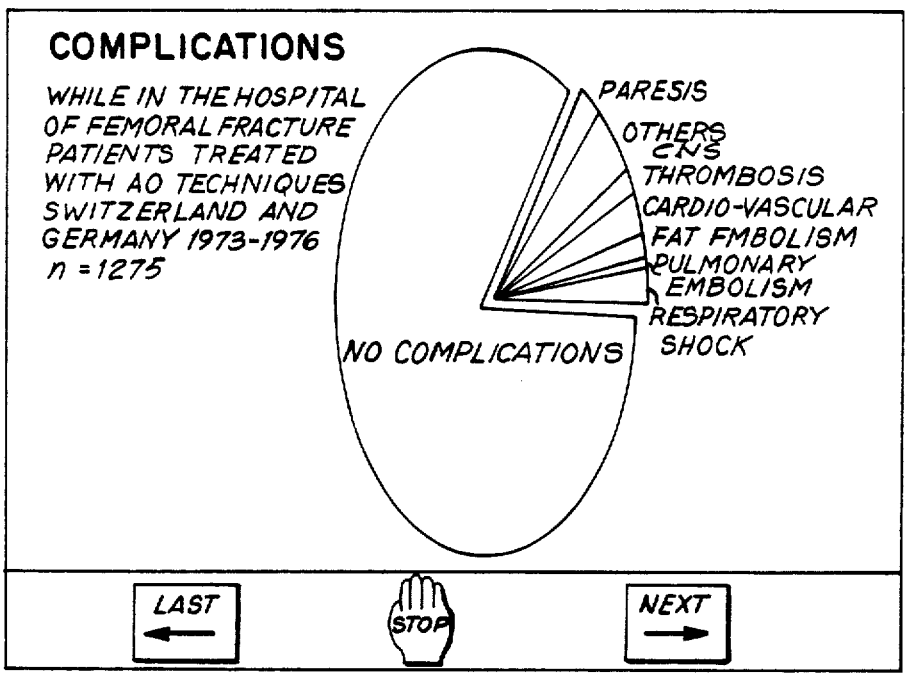
FIG. 17 illustrates a screen which can be used to illustrate to the user of the system possible complications associated with the particular fracture under study.

Finally, when the user is finished with the screen shown in FIG. 16, a further screen, illustrated in FIG. 17, can be displayed to illustrate to the user a statistical summary of complications experienced with patients with similar fractures, if such a data is available.

The program flow will now be described with reference to an example which uses an inference engine developed by Texas Instruments, called Personal Consultant TM Plus, Version 2.0. It will be appreciated, however, that other inference engines, such as those associated with some of the above-mentioned commercially available expert systems could be used as well. Reference will also be made to the following programs and data bases:

| Program or Data Base | Microfiche Appendix |
| --- | --- |
| Application Program | Pages 1–70 |
| Knowledge Base Rules and Parameter Descriptions | Pages 71–93 |
| Procedure Hierarchy | Page 94 |
| Initial Procedure Suggestions | Pages 95–96 (97 not used) |
| Classification Descriptions | Pages 98–102 |
| Batch Files | Pages 103–105 |
| Preexisting Diseases | Page 106 |
| Trauma Descriptions | Page 107 |
| Classification Expansions | Pages 108–109 |

The application program, at pages 1 through 70 of the microfiche appendix, generally corresponds to the application program 12 of FIG. 1. It is written in MICROSOFT C programming language for use on IBM AT ® compatible computers, and makes use of a data base program called BTRIEVE, by SoftCraft, of Austin, Texas, and of a graphics program called ESSENTIAL GRAPHICS, Version 1.5, by Essential Software, Maplewood, New Jersey.

The Knowledge Base Rules and Parameter Descriptions at pages 71 through 93 of the microfiche appendix, form the knowledge base 16 of FIG. 1. The Procedure Hierarchy, Initial Procedure Suggestions, Classification Descriptions, Preexisting Diseases, Trauma Descriptions and Classification Expansion databases form the database 20 of FIG. 1.

To initiate the program the user will type the command "AOPC", which will call the batch file "AOPC-.BAT" found in the batch file listings in the microfiche appendix. That batch file in turn causes the inference engine program to be executed, to thereby create the inference engine, which controls all further program flow. The inference engine first requests the name of the knowledge base with which it is to work, and by responding "AOOA", the name given to the knowledge base of the present example, the inference engine accesses the appropriate knowledge base.

Figure 18:
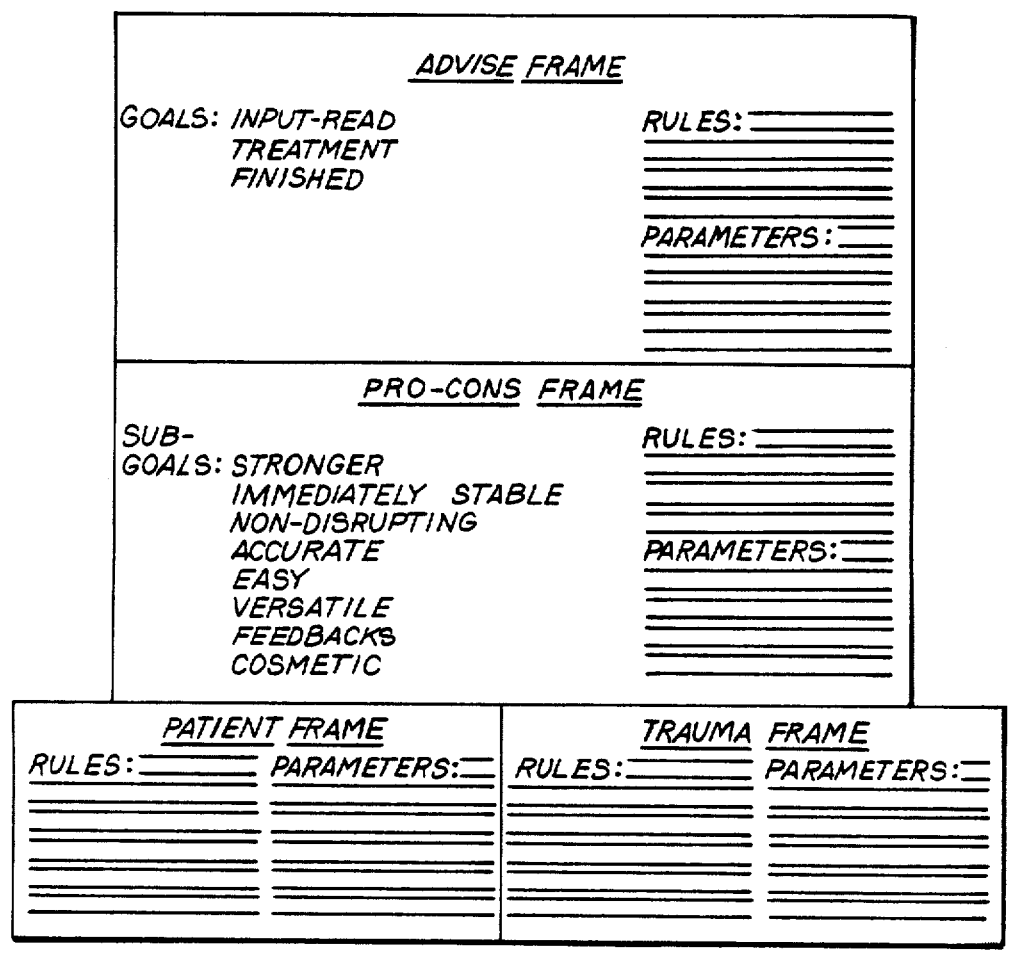
FIG. 18 illustrates the hierarchy of information within the knowledge base of the expert system.

The inference engine first examines a listing of parameters entitled FRAMETYPES in the knowledge base, in order to determine the structure of the knowledge base. The parameter group FRAMETYPES is set forth on page 84 of the microfiche appendix, but the structure it implies is also shown in FIG. 18.

With reference to that figure, the rules and parameters of the knowledge base, and associated "goals", are divided into logical categories, commonly referred to as "frames". In the present example, four such frames exist, namely, ADVISE, PROS-CONS, PATIENT and TRAUMA. The parameter group FRAMETYPES indicates to the inference engine the hierarchy of frames, as shown in FIG. 18. The first, and highest level frame is ADVISE, followed by PROS-CONS, which in turn is followed by the PATIENT and TRAUMA frames, which share the lowest level in the hierarchy. Also shown in FIG. 18 for the ADVISE and PROS-CONS frames are goals associated with each frame. No goals are assigned to the PATIENT and TRAUMA frames.

The rules within each frame are logically grouped according to function. For example, the PATIENT frame contains rules for determining specific characteristics of the patient, for example whether the patient is young or old, whether the patient is osteoporotic, and the like. The rules in the TRAUMA frame determine characteristics of the trauma, for example whether the trauma involves bilateral fractures of weight-bearing bones. The rules within the PROS-CONS frame rely upon the inferences drawn, and the conclusions reached, in the PATIENT and TRAUMA frames. For example, if it is determined from the PATIENT frame that the bone site is osteoporotic, then the rules in the PROS-CONS frame might determine that there is strongly suggestive evidence that a procedure which allows for settling to occur is important. Finally, the rules within ADVISE frame rely upon the inferences and conclusions drawn in the PROS-CONS, PATIENT and TRAUMA frames, and based upon the inferences and conclusions drawn in those frames, the ADVISE frame arrives at a final set of recommended procedures.

The inference engine will inspect the list of frametypes and determine from that list the highest order frame, which in this example is ADVISE. The inference engine then looks at the goals stated for the ADVISE frame. As shown in FIG. 18, the stated goals are INPUT-READ, TREATMENT, and FINISHED. The inference engine, upon instantiating any of the frames shown in FIG. 18, including the ADVISE frame, tries to achieve the stated goals, in the stated order. In the case of the ADVISE frame, the first such goal is INPUT-READ. The inference engine then searches for the paremeter "INPUT-READ" within the parameter descriptions in the knowledge base, and the listing as it appears in the knowledge base (and microfiche appendix) is set forth immediately below, to help facilitate this explanation:

INPUT-READ[ADVISE-PRAMS]

TRANSLATION: (information available from initial system queries)
TYPE: YES/NO
USED-BY RULE026 RULE007 RULE038 RULE039
UPDATED BY: SREFMARK RULE026

The parameter INPUT-READ is indicated as being one of the ADVISE parameters. Its translation, for the convenience of the system designer, is indicated as taking information from initial system quieries. The type of parameter is indicated as being "yes/no", i.e., a single valued variable, as opposed to a variable which can take on numerous values. The INPUT-READ parameter is indicated as being used by Rules 26, 7, 25, 38 and 39, and updated by Rule 26, which is further indicated as being a self-referencing rule, meaning that the parameter "INPUT-READ" is found in both the "if" and "then" portions of the rule, as explained in more detail below.

The inference engine then branches to the rule that updates INPUT-READ, namely Rule 26, which executes a disk operating system call to a batch file INI-TIT.BAT. This batch file, which also appears in the microfiche appendix, calls the application program 12, FIG. 1.

Execution of the application program creates the working files 18, FIG. 1, namely TRAUMA, TISSUE, PATIENT and DISEASE, in response to the information elicited from the user, in combination with the information contained in the databases in database 20. Specifically, the TRAUMA file includes the following parameters:
FRACTURE CLASS
ARTICULAR
INHERENTY STABLE
NUMBER-PEICES
POTENTIALLY STABLE
WEIGHT-BEARING The application program designates the FRACTURE CLASS in the TRAUMA file to be the class of fracture designated by the user in the screen illustrated in FIG. 6, namely classification 31B2.2. The remaining parameters in the TRAUMA file are given values based upon the CLASS EXPANSION database, in database 20, which for each fracture classification provides information as to whether the fracture is articular, inherently stable, etc. It will also be noted that one or more initially indicated treatments are provided by the Initial Procedure Suggestion data base, based upon the fracture classification.

The file TISSUE includes the following parameters:
EXTREMITY
NERVOUS
RESPERATORY
ABDOMINAL
CARDIOVASCULAR
SKIN
COMPLICATIONS
ISS
SOFT TISSUE DAMAGE
OPEN CLASS The first seven parameters of the TISSUE file designated by the application program in response to the information provided by the user in response to the screen illustrated in FIG. 7. The SOFT TISSUE DAMAGE and OPEN CLASS parameters are designated in accordance with the information provided by the user in response to the screen illustrated in FIG. 9. Finally, the injury severity score (ISS) is calculated by the application program, based on the other parameters in the TISSUE file.

The PATIENT file contains the following parameters, each of which is taken directly from the information given by the user in response to the screens illustrated in FIGS. 10 and 11:
AGE
SEX
WEIGHT
HEIGHT
LIFESTYLE/OCCUPATION The DISEASE file contains the following parameters:
HEALING
OSTEOPOROTIC
CONDOLESCENT RISK
SURGERY INTOLERABLE
UNRELIABLE These parameters are either taken directly from the user inputs in response to the screen illustrated in FIG. 12, or through use of the Preexisting Disease database, in database 20, if the user selects one or more of the diseases set forth in the screen illustrated in FIG. 13.

Upon completion of the creation of the working files 18, the application program relinquishes control to the inference engine, which, while still in the ADVISE frame, checks off the INPUT-READ goal of that frame as being completed. The inference engine and processor 10 finds the next goal, TREATMENT, in the ADVISE frame, and searches the knowledge base 16 for the parameter TREATMENT, which is reproduced below:

TREATMENT [ADVISE-PARMS]

TRANSLATION: (the suggested treatment for this orthopedic fracture)
LEGALVALUES: TEXT
TYPE: MULTIVALUED
UPDATED-BY RULE010 RULE005 RULE009 RULE004 RULE002 RULE003 RULE032 RULE008 RULE007

The goal TREATMENT is to determine one or more preferred treatments for the specific patient and trauma. The above listing indicates that the TREATMENT parameter is multivalued and is updated by Rules 10, 5, 9, 4, 2, 3, 32, 8 and 7. The inference engine selects the first rule which updates the TREATMENT parameter, namely Rule 10, and searches the knowledge base for that rule. It should be noted that all rules in the knowledge base must be in either the same frame as the parameter it updates (TREATMENT in this case), or in a lower frame. Rule 10, which is found in the ADVISE frame, is set forth below:

RULE010[ADVISE-RULES]

IF: VERSATILE
THEN: TREATMENT ="X-FIX" CF 3 AND TREATMENT="CAST" CF 7 AND TREATMENT ="TRACTION" CF 7 AND TREATMENT != "PLATE" CF 1 AND TREATMENT != "NAIL" CF 3 AND TREATMENT ="LAG SCREWS" CF 3 AND TREATMENT ="WIRE " CF 3 AND TREATMENT = "OPEN REDUCTION" CF 3

040 treatment that is versatile in its application is important, then there is weakly suggestive evidence (with a certainty factor of 30%) that the suggested treatment for this orthopedic fracture is X-FIX, and there is weakly suggestive evidence (certainty factor of 70%) that the suggested treatment for this orthopedic facture is CAST, and so on. An exclamation point before an equal sign indicates that the stated treatment is not recommended, with a given certainty factor. For example, Rule 10 states that there is weakly suggestive evidence (certainty factor 1%) that the suggested treatment is not PLATE.

The inference engine now tries to determine the truth of the premise of this Rule, namely whether a treatment that is versatile in its application is important. Thus, the parameter VERSATILE becomes the inference engine's new goal. The inference engine 14 searches the knowledge base 16 for the parameter VERSATILE, and that parameter (found in the ADVISE frame) is reproduced below:

VERSATILE[ADVISE-PARMS]

TRANSLATION: (a treatment that's versatile in its application is important)
DEFAULT: (NO)
TYPE: YES/NO USED-BY RULE010
UPDATED-BY RULE041

If a value of VERSATILE cannot, for one reason or another, be calculated, the default value for the parameter is "No". VERSATILE is defined as a single valued parameter (Yes/No), is used by Rule 10 and is updated by Rule 41. The inference engine will search the knowledge base for Rule 41 which is reproduced below:

RULE041[TRAUMA-RULES]

IF:ODD SIZE OR VALUE ISS>30
THEN: VERSATILE CF 60

The inference engine will at this point note that Rule 41 is located within the TRAUMA frame, FIG. 18, rather than in the ADVISE frame, where the parameter VERSATILE is located. At every instance, or "instantiation" in which the inference engine must move from one frame to another, it may only do so through a contiguous frame in the hierarchy, shown in FIG. 18. Thus, in order for the inference engine to move from the ADVISE frame to the TRAUMA frame, it must first instantiate the PROS-CONS frame.

Upon instantiating the PROS-CONS frame, the inference engine selects all of the goals within the PROS-CONS frame as its current set of goals, with the goals being taken in the order listed in the FRAMETYPE file, as shown in FIG. 18. Thus, the parameter STRONGER becomes the next goal, or more properly "subgoal" of the inferenced engine.

The inference engine searches the knowledge base for the parameter STRONGER, in the current frame (PROS-CONS) or a higher frame (ADVISE). The STRONGER parameter is found in the ADVISE frame and is listed below:

STRONGER[ADVISE-PARMS]

TRANSLATION:(a relatively very strong system is important)
DEFAULT: ( NO)
TYPE: YES/NO
USED-BY RULE002
UPDATED-BY RULE011

Since this parameter is updated by Rule 11, the inference engine searches for that rule in the current (ADVISE) or lower frames, Rule 11 will be found in the PROS-CONS frame, and is listed below:

RULE011[PROSCONS-RULES]

IF: BI-WEIGHT

THEN: STRONGER CF 90

The rule states that if the trauma involves bilateral fractures of weight-bearing bones, there is strongly suggestive evidence (90%) that a relatively strong system is important. The inference engine must now find the parameter BI-WEIGHT in the knowledge base, and the parameter is defined therein as follows:

BI-WEIGHT[PROSCONS-PARMS]

TRANSLATION: (the trauma involves bilateral fractures of weight bearing bones)
PROMPT: YES
TYPE: YES/NO
USED-BY RULE 011 RULE030
UPDATED-BY: RULE040

The designation "PROMPT: YES" indicates that the inference engine will prompt the user to provide or confirm this information, if necessary. Since the parameter BI-WEIGHT is updated by Rule 40, the inference engine searches the knowledge base for Rule 40, which is found in the TRAUMA frame, as follows:

RULE040[TRAUMA-RULES]

IF: VALUE EXTR<4
THEN:! BI-WEIGHT

This rule states that if the extremity value is less than four, then the trauma does not involve bilateral fractures of weight-bearing bones. The inference engine searches the knowledge base for the parameter EXTR, and it is found in the TRAUMA frame, as follows:

EXTR[TRAUMA-PARMS]

TRANSLATION: (the extremity score from the health trauma index)
TYPE: SINGLEVALUED
USED-BY RULE040
UPDATED-BY RULE039

Since this parameter is updated by Rule 39, the inference engine searches the knowledge base for Rule 39, which is located in the TRAUMA frame, as follows:

RULE039[TRAUMA-RULES]

Figure 19:
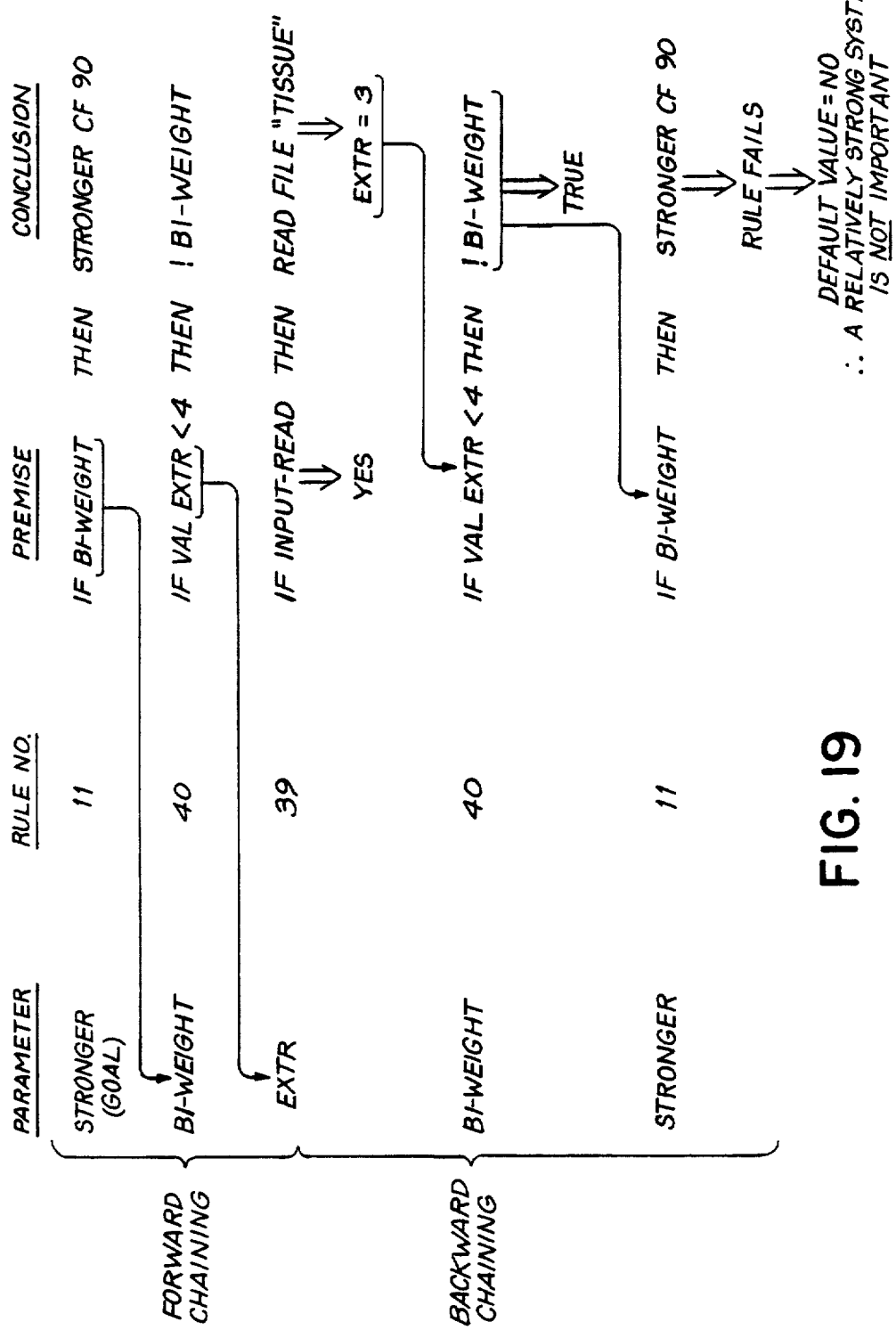
FIG. 19 is a chart illustrating the forward and backward chaining employed by the inference ebgine, in accordance with the present invention.

IF: INPUT-READ
THEN: READ*FRAME "tissue" QUOTE (EXTR NERV RESP ABDM CARD
SKIN COMP ISS SOFT-TISSUE-DAMAGE OPEN-CLASS) TALLY This rule states that if information is availble from the initial system quiries, then the stated data are to be read from the file TISSUE. Since the premise is true, namely that information is available from the initial system queries, then the inference engine reads the stated values from the file TISSUE in the working files 20, FIG. 1, including the value of the extremity score EXTR. Having determined the value of the extremity score, the inference engine is now ready to arrive at a value for the sub-goal STRONGER. This is accomplished through a process called "backward-chaining" and involves stepping back through the path that resulted in the value for the parameter EXTR. With reference to FIG. 19, it will be seen that the value of EXTR was determined by invoking Rule 11, then Rule 40, and then Rule 39, through a "forward chaining" process. The backward chaining takes these rules in the reverse order: Rule 39, then Rule 40, then Rule 11. From Rule 39, Rule 40 is invoked, namely that if the extremity value is less than four, then the trauma does not involve bilateral fractures of weight bearing bones. Since the value of the extremity score is three, then the rule is satisfied, and the trauma does not involve bilateral fractures of weight-bearing bones. The next rule in the chain, Rule 11, is tested, and since the premise of bilateral fractures of weight-bearing bones is not true, then Rule 11 fails and no action is taken. At this point, the inference engine will return to the parameter definition of STRONGER to see whether it is updated by any rules in addition to Rule 11, and if so, tests those rules in the same manner, to see whether they assign a value to the parameter. Since there are no other rules which update the parameter STRONGER, the inference engine selects for the parameter STRONGER the default value, in this case "NO". In essence, the inference engine has just concluded that a relatively strong system is not important.

It should be noted that for single-valued parameters, such as STRONGER, which require an answer in the form of a YES/NO, MALE/FEMALE or YOUNG/OLD, the inference engine will try all of the rules which update that parameter until the rule tests true, and no further rules which update the parameter will be tested. However, for multiply valued parameters, the inference engine will repeat the process for all of the rules which update that parameter, until all such rules are exhausted. In the present example, the only multiply valued parameter is TREATMENT—all others are single valued.

Returning to FIG. 18, it will be seen that the first listed subgoal in the PROS-CONS frame, namely STRONGER, has been determined, and the inference engine will proceed with the remaining sub-goals in the order listed. However, for the purposes of illustrating the present example, it will now be assumed that all of the sub-goals preceeding VERSATILE have been satisified, and the explanation will proceed with the sub-goal VERSATILE.

The inference engine searches the knowledge base for the parameter VERSATILE and its parameter description, stated above, indicates that VERSATILE is updated by Rule 41, also stated above. Rule 41 states that if the patient is either very large or the injury severity score is greater than 30, there is evidence, having a certainity factor of 60%, that a treatment that is VERSATILE in its application is important. The inference engine then searches for the parameter ODD-SIZE, and will find the following parameter description in the PROS-CONS frame:

ODD-SIZE[PROSCONS-PARMS]

TRANSLATION: (the patient is very large)
PROMPT: YES
TYPE: YES/NO
USED-BY RULE041
UPDATED-BY RULE021 RULE022

The inference engine will then search for the first rule that updates the parameter, namely Rule 21, which is found in the PATIENT frame as follows:

RULE021[PATIENT-RULES]

IF: VALUE HEIGHT>198 OR VALUE WEIGHT=136
THEN: ODD-SIZE

Thus, if the height of the patient is greater than 198 centimeters or the weight of the patient is greater than 136 kilograms, then the patient is considered to be very large. The inference engine then searches the knowledge base for the parameter HEIGHT which is found in the patient frame as follows:

HEIGHT[PATIENT-PARMS]

TRANSLATION: (the height of the patient in centimeters)
PROMPT: YES
EXPECT: POSITIVE-NUMBER
RANGE: (30-230)
TYPE: SINGLEVALUED
USED-BY: RULE021 RULE022
UPDATED-BY: RULE025

The inference engine then searches for Rule 25 which is found in the patient frame, as follows:

RULE025[PATIENT-RULES]

IF: INPUT-READ
THEN: READ*FRAME "patient" QUOTE (AGE SEX WEIGHT HEIGHT LIFEOCC) TALLY The inference engine, in response to reading Rule 25 will read from the file PATIENT in the working files 20, FIG. 1, the stated parameters, including HEIGHT and WEIGHT.

The inference engine will then chain back to Rule 21 (stated above) to see whether the ODD-SIZE premise is true. For this example, it will be assumed that the patient's height is greater than 198 centimeters or that the patient's weight is greater than 136 kilos, and therefore ODD-SIZE is true. Had this not been the case, the inference engine would have returned to the parameter description for ODD-SIZE (stated above) to find that it is also updated by Rule 22, to see whether Rule 22 would yield a true value for ODD-SIZE. However, since Rule 21 yielded a true value, and since the ODD-SIZE parameter is single-valued, the inference engine can ignore Rule 22.

Continuing the backward chaining process, the inference engine returns to Rule 41, and since ODD-SIZE is true, then it is also true with a 60% certainty factor that a treatment that is VERSATILE in its application is important.

Having determined the value of the sub-goal VERSATILE, the remaining sub-goals are determined in the same manner, and then the inference engine returns to the rule which originally instantiated the PROS-CONS frame, namely Rule 41. However, Rule 41 has already been satisfied, so the infernce engine chains back to the previous rule, namely Rule 10.

Rule 10 (stated above) starts by indicating that there is a 3% certainty factor that the suggested treatment is an X-FIX, if a VERSATILE treatment is important. In this example, it was determined that a VERSATILE treatment was indicated as being important with a certainty factor of 60%. The certainty factor of 3% stated for the X-FIX treatment in Rule 10 is therefore multiplied by the 60% certainty factor that a VERSATILE treatment is important, and that result is added to a number related to the previous value of X-FIX if any exists, either from a previous calculation of the same type, from a different rule which assigned a value to X-FIX, or from a value assigned to the initial treatments selected by the Initial Procedure Suggestions data base, based on the fracture classification, as described above. The updated total for X-FIX as calculated by Rule 10 is related to these quantities according to well known formulas employed by the commercially available inference engines, or for example, the formulas stated in U.S. patent 4,648,044 to Hardy et al. The remaining values of the parameters CAST, TRACTION, PLATE, and the others set forth in Rule 10 are calculated in the same manner, based on the 60% certainty factor associated with a VERSATILE treatment and any previous value for the particular parameter.

After processing Rule 10, the inference engine returns to the parameter which originally invoked it, namely TREATMENT, which is stated above. The next rule which updates the TREATMENT parameter is Rule 5, which is as follows:

RULE500[ADVISE-RULES]

IF: ACCURATE
THEN: TREATMENT ="X-FIX" CF 13 AND TREATMENT ="CAST" CF 0 AND TREATMENT ! ="TRACTION" CF 17 AND TREATMENT ="NAIL" CF 23 AND TREATMENT ="LAG SCREWS" CF 30 AND TREATMENT ="WIRE" CF 0 AND TREATMENT ! ="JOINT REPLACEMENT" CF 17 AND TREATMENT ! ="OPEN REDUCTION" CF 20 AND TREATMENT ="PLATE" CF 30.

The premise of Rule 5 is the need for a relatively accurate result, and the inference engine performs the same chaining functions necessary to determine whether an accurate result is necessary, and with what certainty factor, in a manner similar to that performed for the parameter VERSATILE. After determining a certainty factor for the parameter ACCURATE, the inference engine performs the same mathematical functions with the certainty factors associated with the parameters listed in Rule 5, and with the certainty factor for the parameter ACCURATE, and those values are added to the previous values, if any, for each of the possible treatments.

Returning to the description of the parameter TREATMENT, the same procedure is followed for Rules 9, 4, 2, 3, 32, 8 and 7, until final values are generated for each of the possible treatments referenced in those rules. At the conclusion of each of those rules, the inference engine is done with the goal TREATMENT, and the next goal in the ADVISE frame is FINISHED. The inference engine will search the knowledge base for the description of the parameter FINISHED, which functions to call an application program called FINAL (or FINCUR, if a touch screen is not available). This program presents the debriefing screens illustrated in FIGS. 16 and 17, based on a selected number of the most highly indicated treatments, namely those with highest values.

In addition to calculating the values for each treatment in accordance with the procedure outlined above, additional processing, in accordance with the present invention, may be made in order to increased the likelihood that the proper treatment or treatments will be selected.

Figure 20:
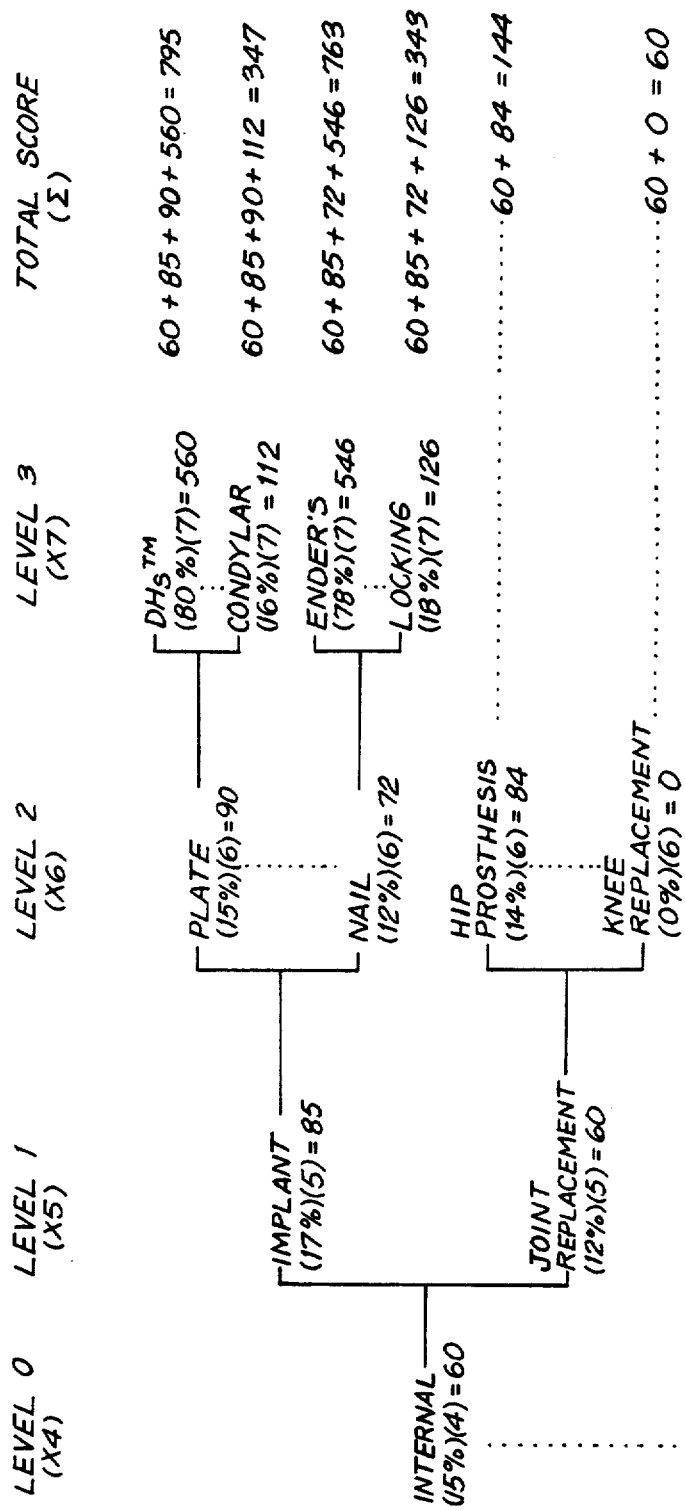
FIG. 20 is an illustration of a techanique for determining the optimal treatment, based on certainty factors and the hierarchy of treatment suggestions.

Specifically, each of the recommended treatments forms part of hierarchy of suggested treatments, as indicated by the file Procedure Hierarchy data base in the working files 20. A chart illustrating the hierarchy for some selected treatments is shown in FIG. 20. The broadest treatment is INTERNAL, and two types of internal treatments are IMPLANT and JOINT REPLACEMENT. Furthermore, two types of implants are PLATE and NAIL. Likewise, two types of plates are DHS TM, CONDYLAR, and two types of nail treatments are ENDER'S and LOCKING. Finally, under joint replacement, the two treatments are HIP PROSTHESIS and KNEE REPLACEMENT.

The treatment hierarchy shown in FIG. 20 has four levels, numberd 0 through 3, as shown. The broad category of INTERNAL treatments is at level 0, IMPLANT and JOINT REPLACEMENT are at level 1, PLATE, NAIL, HIP PROSTHESIS and KNEE REPLACEMENT are at level 2 and DHS TM, CONDYLAR, ENDER'S and LOCKING are at level 3. A total score for each of the most specific treatments (DHS TM, CONDYLAR, ENDERS, LOCKING, HIP PROSTHESIS and KNEE REPLACEMENT) can be determined as follows. The certainty factors associated whit each of the treatments shown in FIG. 20, as determined by the rules implicated by the TREATMENT goal and indicated in parenthesis underneath each treatment, are multiplied by a weghting factor, such that the certainty factors associated with the more specific treatments are more heavily weighted that those associated with the broader treatment categories. In the present example, a weighting factor equal to four plus the number of the level of treatment, equals the weighting factor. As shown the certainty factors are multiplied by 4, in level 0, by 5 in level 1, 6 in level 2, and so on. It should be noted that this specific weighting function is exemplary, and others may be found to be more suitable for particular applications.

After multiplying the certainty factor of each treatment suggestion by the weighting factor, the individual totals for each of the most specific (highest level) treatments are added to the individual totals in each of its parent categories, up to and including the broadest category (level 0). For example, the individual total for DHS TM, is 560. This figure is added to the figure for its parent (PLATE=90), its grandparent (IMPLANT=85) and its great-grandparent INTERNAL =60), to yield a total score of 795. The higher the score, the more highly the specific treatment is recommended. A slected number of the most highly recommended treatments may be displayed, as illustrated in FIG. 16. It will be noted that in FIG. 16, the information within icons 66, 68, 70 and 72 generally indicate treatment hierachy for the respective treatment.

Thus, the present invention provides a highly sophisticated system for providing a set of recommended treatments for specific catergories of physical trauma, using state-of-the-art expert system technology. Various changes and variations to the present invention will occur to those skilled in the art in view of the foregoing description. For example, other types of physical trauma, in addition to orthopedic fractures will find equally suitable implementation using the techniques in accordance with the present invention. It is also intended that the particular classification of orthopedic fractures, treatments, and other database information be exemplary, rather than limiting, and that all such changes and variations be encompassed so long as the present invention is employed, as defined by the following claims.

What is claimed is:

1. An expert system for providing to a user one or more suggested treatments for a patient with physical trauma, comprising:

a computing device having a memory;
a plurality of data bases in the memory including graphical illustrations of different types of physical trauma, and a knowledge base having rules for relating trauma and patient characteristics to treatments for said different types of physical trauma;
an application program, for execution in the computing device, for interactively displaying a series of screens including at least some of the graphical illustrations, to thereby elicit responses from the user concerning the specific type of physical trauma and specific characteristics of the patient, to thereby produce a further data base containing said trauma and patient characteristics; and
an inference engine program, for execution in the computing device, for use with said rules and said further data base, for selecting the one or more suggested treatments by stepping through a forward chaining sequence of rules relating to a particular treatment, and then by stepping through a backward chaining sequence of rules, the reverse of the forward chainin sequence, in which said rules are tested, based on said trauma and patient characteristics, to determine the desirability of said particular treatment;
the application program presenting the suggested treatments to the user after execution of the inference program.

2. An expert system for providing to a user one or more suggested treatments for a patient with an orthopedic fracture, comrising:

a computing device having a memory;
a plurality of data base in the memory, including graphical illustrations of different classifications of orthopedic fractures; and a knowledge base having rules for relating trauma and patient characteristics to treatments for said different types of physical trauma;
an aplication program, for execution by the computing device, for interatively displaying a series of screens on a display, including at least some of the graphical illustrations, to thereby elicit responses from the user concerning the specific classification of orthopaedic fracture, and specific characteistics of the patient; to thereby produce a further data base containing said trauma and patient characteristics; and
an inference engine program, for execution in the computing device, for use with said rules and said further data base, for selecting the one or more suggested treatments by stepping through a forward chaining sequence of rules relating to a particular treatment, and then by stepping through a backward chaining sequence of rules, the reverse of the forward chaining sequence, in which said rules are tested, based on said trauma and patient characteristics, to determine the desirability of said particular treatment;
the application program presenting the suggested treatments to the user after execution of the inference program.

3. A method for providing to a user a suggested treatment for a patient having physical trauma, comprising the steps of:

creating at least one knowledge base containing rules that relate different types of physical trauma characteristics and patient characteistics to different types of treatments for physical trauma;
eliciting information from said user concerning characteristics of said patient including the type of physical trauma substained by said patient, to thereby develop at least one database containing patient and trauma characteristics;

applying said knowledge base and database to a computer; and using said computer to infer the apropriate treatment for said patient from said rules and said database, by forward chaining, in which a sequence of rules relating to a particular treatment is established, and backward chaining, in which said sequence of rules es reversed and said rules are tested based on said trauma and patient characteristics, to determine the desirability of said particular treatment.

4. The method of claim 3, wherein said step of creating said knowledge base includes the step of creating rules that relate said trauma and patient characteristc to characteristics of said treatments, said step of forward chaining establishes a sub-sequence of rules relating to a particular treatment characteristic, and said step of backward chaining reverses said subsequence of rules, and testes said sub-sequence of rules based on said trauma and patient characteristics, to thereby determine the desirability of said particular treatment characteristic.

5. The method of claim 3, wherein said step of sliciting information concerning the type of physical trauma sustained by said patient includes the step of interactively desplaying different classifications of trauma to said user.

6. The method of claim 5, wherein the step of interactively displaying includes the step of displaying graphical representations of said classifications of trauma.

7. The method of claim 6, wherein said differeent types of trauma are orthopedic fractures.

8. The method of claim 4, wherein the step of using a computer includes the step of employing an inference engine to infer the appropriate treatment.

9. The method of claim 5, wherein the step of eliciting information includes the use of a touch-screen CRT.

10. The method of claim 3, wherein said step of using the computer to infer the appropriate treatment further includes the steps of assingning a value to each of a plurality of possible treatments, and adjusting said values according to a treatment hierarchy, wherein values assigned to specific treatments are more heavily weighted than values assigned to general treatments.

11. An expert system for providing to a user a suggested treatment for a patient having physical trauma, comprising:

at least one knowledge base containing rules that relate different types of physical trauma characteristics and patient characteristics to different types of treatments for physical trauma, a computer for receiving said knowledge base and information from said user concerning characteristics of said patient, including the type of physical trauma sustained by said patient, to thereby develop at least one database containing patient and trauma characteristics; and an processor within said computer to infer the appropriate treatment for said patient from said rules and said database by forward chaining, in which a sequence of rules relating to a particular treatment is established, an then by backward chaining, in which said sequence of rules is reversed and said rules are tested based on said trauma and patient characteristics, to determine the desirability of said particular treatment.

12. The expert system of claim 11, wherein said knowledge base includes rules that relate said trauma and patient characteristics to characteristics of said treatments, said forward chaining establishes a sub-sequence of rules relating to a particular treatment characteristic, and said backward chaining reverses said sub-sequence of rules an tests said sub-sequence of rules based on said trauma and patient characteristics, to thereby determine teh desirability of said particular treatment characteristic.

13. The expert system of claim 11, wherein said computer elicits information concerning the type of physical trauma sustained by said patient by interactively displaying different classification of trauma to said user.

14. The expert system of claim 13, wherein said computer displays graphical representations of said classifications of trauma.

15. The expert system of claim 14, wherein said different types of trauma are orthopedic fractures.

16. The expert system of claim 13, wherein said computer employs a touch-screen CRT.

17. The expert system of claim 11, wherein said computer assigns a value to each of a plurality of possible treatments, and adjusts said values according to a treatment hierarchy, wherein values assigned to specific treatments are more heavily weighted than values assigned to general treatments.

* * * * *

UNITED STATES PATENT AND TRADEMARK OFFICE
CERTIFICATE OF CORRECTION

PATENT NO. : 4,839,822
DATED : June 13, 1989
INVENTOR(S) : Kenneth Dormond, Robert J. Friedman It is certified that error appears in the above-identified patent and that said Letters Patent is hereby corrected as shown below:

In the Abstract line 12    "types" should read --type--

In the Specification

| | |
|---|---|
| Col. 1, line 31 | "workpiece" should read --workplace-- |
| Col. 1, line 49 | After "Instruments," insert --Inc.,-- |
| Col. 1, line 57 | After "4,591,983" add --to-- |
| Col. 2, line 45 | Delete second occurrence of the word "to" |
| Col. 3, line 23 | Before "treatment" insert --suggested-- |
| Col. 3, line 32 | "ebgine" should read --engine-- |
| Col. 3, line 34 | "techanique" should read --technique-- |
| Col. 3, line 51 | "CTR" should read --CRT-- |
| Col. 4, line 3 | "relevent" should read --relevant-- |
| Col. 5, line 64 | After "neck," insert --or-- |
| Col. 6, line 12 | "addition" should read --adduction-- |
| Col. 6, line 23 | "illustrated" should read --illustrating-- |
| Col. 7, line 61 | "osteoportic" should read --osteoporotic-- |

UNITED STATES PATENT AND TRADEMARK OFFICE
CERTIFICATE OF CORRECTION

PATENT NO. : 4,839,822
DATED : June 13, 1989
INVENTOR(S) : Kenneth Dormond, Robert J. Friedman It is certified that error appears in the above-identified patent and that said Letters Patent is hereby corrected as shown below:

| | |
|---|---|
| Col. 8, line 19 | After "data" insert --base-- |
| Col. 9, line 39 | After "within" insert --the-- |
| Col. 9, line 66 | After "RULE007" insert --RULE025-- |
| Col. 11, line 62 | Before "treatment" delete "040" and insert --An interpretation of the above rule is as follows. If a-- |
| Col. 12, lines 21, 60 and 61 | After "BY" insert --:-- |
| Col. 13 line 14 after | "by" insert --:--. |
| Col. 13, line 14 | "RULE 011" should read --RULE011-- |
| Col. 13, lines 36,37 | After "BY" insert --:-- |
| Col. 14, lines 54,55 | After "BY" insert --:-- |
| Col. 14, line 63 | "=" should read ">" |
| Col. 16, line 12 | "RULE500" should read --RULE005-- |
| Col. 16, line 54 | "increased" should read --increase-- |
| Col. 16, line 67 | Before CONDYLAR insert --and-- |
| Col. 17, line 14 | "whit" should read --with-- |
| Col. 17, line 20 | "that" should read --than-- |
| Col. 17, line 37 | Before "INTERNAL" insert --(-- |

UNITED STATES PATENT AND TRADEMARK OFFICE
CERTIFICATE OF CORRECTION

PATENT NO. : 4,839,822

DATED : June 13, 1989

INVENTOR(S) : Kenneth Dormond, Robert J. Friedman

It is certified that error appears in the above-identified patent and that said Letters Patent is hereby corrected as shown below:

| | |
|---|---|
| Col. 17, line 38 | Before "score" insert --total-- |
| Col. 17, line 42 | Before "treatment" insert --the-- |

<u>In the Claims</u>

| | |
|---|---|
| Col. 18, line 18 | "chainin" should read --chaining-- |
| Col. 18, line 30 | "base" should read --bases-- |
| Col. 19, line 11 | "es" should read --is-- |
| Col. 19, line 16 | "characteristc" should read --characteristics-- |
| Col. 19, line 22 | "testes" should read --tests-- |
| Col. 19, line 27 | "slicit-" should read --elicit--- |
| Col. 19, line 36 | "differeent" should read --different-- |
| Col. 20, line 14 | "an" should read --a-- |
| Col. 20, line 31 | "teh" should read --the-- |
| Col. 20, line 36 | "classification" should read --classifications-- |

UNITED STATES PATENT AND TRADEMARK OFFICE
CERTIFICATE OF CORRECTION

PATENT NO. : 4,839,822

DATED : June 13, 1989

INVENTOR(S) : Kenneth Dormond, Robert J. Friedman

It is certified that error appears in the above-identified patent and that said Letters Patent is hereby corrected as shown below:

Col. 18, line 27, "comrising" should read --comprising--.

Signed and Sealed this

Twenty-second Day of May, 1990

Attest:

HARRY F. MANBECK, JR.

*Attesting Officer*          *Commissioner of Patents and Trademarks*